United States Patent [19]

Brunet

[11] Patent Number: 4,643,721
[45] Date of Patent: Feb. 17, 1987

[54] MULTIPLE COMPARTMENT AMPULE FOR AUTOMATIC HYPODERMIC SYRINGES

[75] Inventor: Patrice Brunet, Neuilly-sur-Seine, France

[73] Assignee: Poutrait-Morin, Aubervilliers, France

[21] Appl. No.: 798,439

[22] Filed: Nov. 15, 1985

[30] Foreign Application Priority Data

Nov. 20, 1984 [FR] France .................. 84 17672

[51] Int. Cl.⁴ .................................... A61M 5/08
[52] U.S. Cl. ......................... 604/191; 604/203
[58] Field of Search .............. 604/191, 200–205, 604/87, 88, 90, 89

[56] References Cited

U.S. PATENT DOCUMENTS

| | | | |
|---|---|---|---|
| 2,939,459 | 6/1960 | Lazarte et al. | 604/203 |
| 3,368,558 | 2/1968 | Sarnoff et al. | 604/203 |
| 3,838,689 | 10/1974 | Cohen | 604/90 |
| 3,911,916 | 10/1975 | Stevens | 604/191 |
| 4,394,863 | 7/1983 | Bartner | 604/191 |
| 4,424,057 | 1/1984 | House | 604/88 |

Primary Examiner—John D. Yasko
Attorney, Agent, or Firm—Charles E. Brown; Charles A. Brown

[57] ABSTRACT

An ampule for an automatic hypodermic syringe comprises at least two axially aligned and hermetically separated compartments containing respective medicated substances. A nipple member is disposed at one end of the ampule. A needle holder is slidably mounted in said nipple member and supports a hollow needle. An intermediate partition normally hermetically separates the two compartments. The intermediate partition has a valve member adapted to open a path of flow through the intermediate partition to bring the second of the compartments into communication with the needle hollow after a first of the compartments is substantially emptied. Preferably, there are two intermediate partitions and three compartments.

12 Claims, 5 Drawing Figures

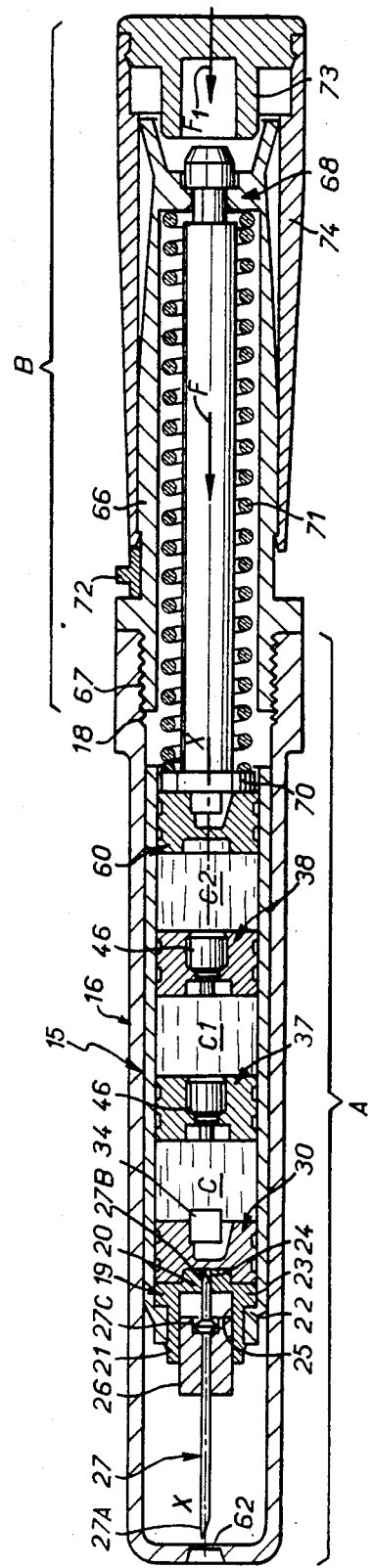
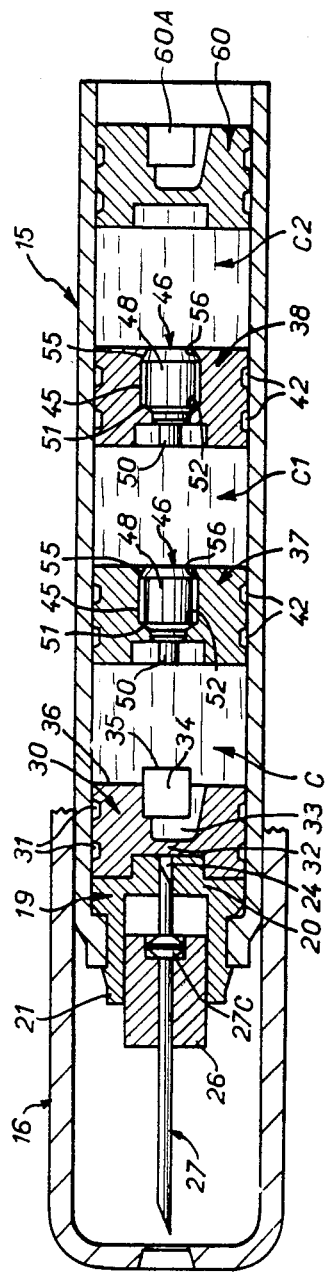
FIG.1
FIG.2

MULTIPLE COMPARTMENT AMPULE FOR AUTOMATIC HYPODERMIC SYRINGES

FIELD OF THE INVENTION

The present invention relates to hypodermic syringes and more particularly automatic syringes having multiple compartment ampules for injecting more than one medicated substance or drug into a patient.

DESCRIPTION OF THE PRIOR ART

There has already been proposed syringes of the above type comprising an ejection means or drive mechanism housed in a first casing and an ampule mounted for displacement in a second casing connected to the first casing. In such a syringe the drive mechanism is normally locked in a standby position in which the ampule is retracted and may be released so that the ampule is suddenly driven from its retracted to its advanced position.

During displacement of the ampule inside the second casing the needle pierces both a cap or membrane provided in the second casing and a zone of reduced strength formed in the forward end of ampule, and the front end of the needle penetrates the skin of the patient at the desired location to administer the medicated substance.

After injection of the substance the second casing which contains the used ampule is disconnected from the first compartment and is discarded. The drive mechanism is re-usable and may be coupled to another second casing accommodating a new ampule ready for use.

Such a syringe was disclosed in French Pat. No. 1,320,820 issued Feb. 4, 1963.

It will be readily noted that the second casing houses an ampule containing one medicated substance so that the use of such an ampule is limited by the fact that frequently it is necessary to administer to a patient a mixture of at least two medicated substances.

Some medicated subtances may be premixed but very often such premixed medicated substances have relatively short shelf lives. Other medicated substances do not admit of being premixed and therefore it is necessary to mix them just prior to administration to the patient.

Automatic syringes had been proposed in which the ampule is provided with at least two compartments each containing a different medicated substance and the ampule is provided with means for premixing the substances just prior to injection. Such an arrangement is taught in U.S. Pat. Nos. 3,572,366 and 3,182,660.

But in this case too there are drawbacks due to the fact that it is not always desirable to mix the medicated substances even just prior to their injection.

OBJECT AND SUMMARY OF THE INVENTION

An object of the invention is to militate against the drawbacks of known automatic syringes as outlined above and to provide a novel ampule eliminating or substantially reducing such drawbacks.

According to the invention there is provided an ampule for an automatic hypodermic syringe comprising at least two compartments adapted to receive respective medicated substances. At one extremity of the ampule is a free end in which a nipple member having a hollow needle is mounted for sliding movement between a standby position and an operative or injecting position. The novel ampule is characterized by the two compartments being separated by an intermediate partition or piston between two end partitions or pistons, the intermediate partition or piston being provided with a valve means adapted to be controlled in order to bring a full compartment into communication with the needle via a previously emptied compartment.

According to another feature of the invention the end partition or piston closest to the needle comprises a depression and an actuator which is adapted to operate the valve means from its closed position to its open position.

According to a preferred embodiment the ampule comprises a plurality of intermediate partitions or pistons, for example two such intermediate partitions or pistons defining three compartments between the end partitions or pistons. The valve means in the first intermediate wall portion closest to the needle being adapted to actuate the valve means of a second intermediate partition or piston to its open position when the compartment between the front end partition or piston and the first intermediate partition or piston is substantially empty.

With a multiple compartment ampule according to the invention associated with a drive mechanism a patient may be automatically injected with a plurality of different medicated substances in succession, each one of the medicated substances being in metered quantities and administrated separately.

These and other features and advantages of the invention would become more apparent from the description which follows, given by way of example, with reference to the accompanying drawings.

BRIEF DESCRIPTION OF THE DRAWINGS

FIG. 1 shows an axial sectional view of an automatic hypodermic syringe comprising a multiple compartment ampule, in accordance with the invention;

FIG. 2 shows, in axial section, the ampule taken on its own, with its protective casing partially cut away.

DESCRIPTION OF THE PREFERRED EMBODIMENT

Figure 3:
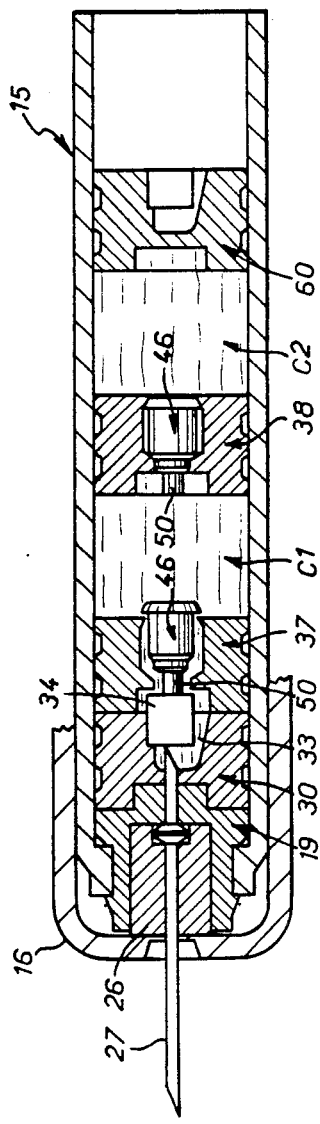
FIGS. 3, 4 and 5 are views similar to that of FIG. 2 illustrating the operation of the ampule.
Figure 4:
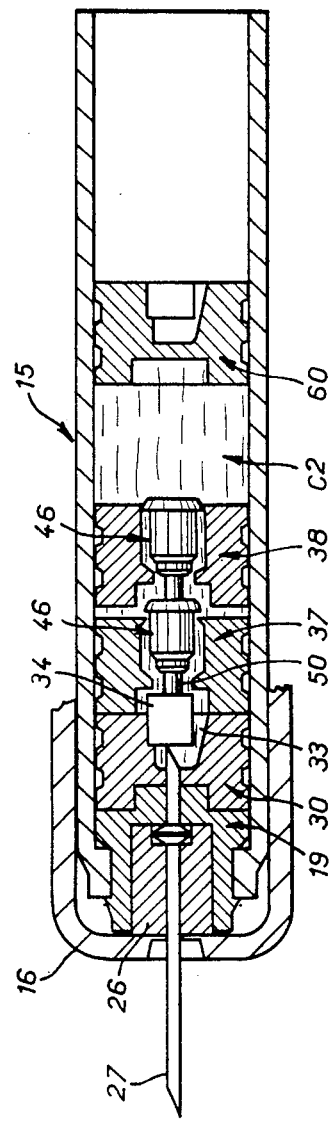
Figure 5:
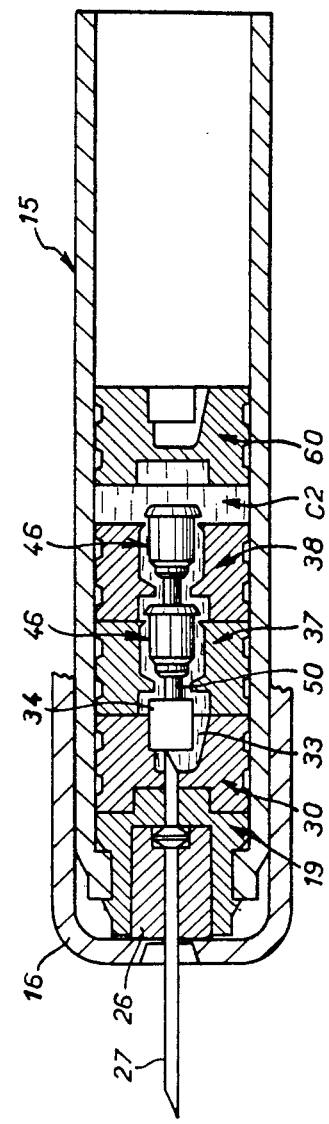

As illustrated in FIG. 1, the novel hypodermic syringe, according to the invention, comprises a front part generally designated by reference A and a rear part generally designated by reference B, the front and rear parts being detachably connected to each other. The rear part B, known per se, which will be described in greater detail hereinbelow, and generally comprises a drive mechanism which has a rest or standby position and an operative or injecting position in which the medicated liquid substance is injected. According to the invention the front part A comprises an ampule designated generally by reference 15 and is of overall right cylindrical configuration having an axis X—X.

The ampule 15 is initially enclosed in a casing 16 hermetically sealed by a stopper (not illustrated) threadedly engageable with screwthread 18. The stopper is removed for attachment of the casing 16 to the drive mechanism. At the end of the casing 16 remote from the screwthread 18 a nipple member 19 is accommodated, comprising a transverse wall 20 and an axially extending skirt 21. The nipple member 19 is in abutment by the cooperation of an annular shoulder 22 of reduced diameter at the front end of the ampule 15 with an annular collar 23 at the junction between the transverse wall 20 and the skirt 21 of the nipple member. The nipple member 19 further comprises in its transverse wall 20 an axial channel 24 communicating with the axial bore 25 slidably mounting a needle holder 26 carrying a hollow needle 27. The hollow needle 27 itself has opposed tapered ends 27A and 27B and an intermediate annular collar 27C accommodated in a corresponding recess in the needle holder 26. The transverse wall 20 of the nipple member 19 defines a support for the first or front end partition or piston 30 which has at least one annular seal 31 at its periphery (FIG. 2). The end partition or piston 30 has a central web 32 of reduced thickness opposite the axial channel 24 in the nipple member 19. The front end partition or piston 30 also has a central recess 33 and an actuator 34 protruding rearwardly behind the rear face 36 of the front end partition or piston 30.

The ampule 15 is designed to provide at least two hermetically separated compartments adapted to receive metered quantities of medicated substance. As illustrated, the ampule 15 comprises, axially spaced from the first or front end partition or piston 30, two intermediate partitions or pistons 37 and 38 each of which is equipped with valve member along the X—X axis of the ampule and at least one annular seal 42 at their peripheries.

In the illustrated embodiment each of the valve members 46 is accommodated in an axial recess 45 of the associated intermediate partition or piston 37, 38. The valve member 46 is of generally cylindrical configuration with an outwardly tapering frustoconical rear surface 55 cooperating with a complementarily shaped seat 56 in the associated intermediate partition or piston 37,38, an outwardly tapering frustoconical forward surface 51 adapted to cooperate with a complementarily shaped seat 52 in the intermediate partition or piston and a forwardly extending valve operator 50.

It will be noted that seats 52 and 56 are configured and longitudinally spaced from each other to axially mount and immobilize the valve member 46 as long as the valve operator 50 is not actuated. Each of the intermediate partitions or pistons 37,38 is made of resilient material so that the lip defining the annular seat 55 can resiliently deform and then resiliently resume its rest position.

As for the other second or rear end partition or piston 60 remote from the nipple member 19, it has a structure similar to that of the front end partition or piston 30 except for the actuator or abutment 60A which does not protrude rearwardly beyond the rear face of the partition 60.

After filling in succession each of the compartments C,C1,C2 with the desired medicated substance and sealingly closing the ampule 15 by means of the second end partition or piston 60, the ampule 15 is inserted inside the casing 16. With regard to the casing 16 it will be noted that it comprises at its initially closed front end a perforable central web 62 of reduced thickness and at the other end the threaded bore having screwthread 18 threadedly engageable with the screwthread 67 on the drive mechanism after the stopper is removed.

Such a drive mechanism essentially comprises a body 66 having at one end the screwthread 67 complementary to screwthread 18 on a casing 16 and at the other end retaining means 68 adapted to maintain the drive member 70 under the bias of the coil spring 71. The drive mechanism further comprises a safety ring 72 adapted to prevent actuation of the push button 73 disposed in the rear end of side wall 74, until the safety ring 72 has been removed.

The push button 73 has a hollow cylindrical projection engageable with a flaring distal end of body 66 to cam the retaining means radially out of engagement with the corresponding necked portion of the drive member 70, freeing the latter to permit its axial displacement under the action of coil spring 71. The construction and operation of such driving means are well known by those skilled in the art and therefore will not be described in greater detail herein.

To operate the automatic hypodermic syringe comprising an ampule 15 and a drive member as illustrated in FIG. 1, the clinician or operator first removes the safety ring 72 and then positions the front end of the casing 16 at the appropriate location on the patient's body and then presses the push button 73 which releases the retaining means 68 whereby the spring 71 which thrusts the ampule 15 forwardly.

During the forward displacement of the ampule 15 the needle 27 first pierces the web 62 since the mechanical strength of web 62 is less than that of web 32 of the front end partition or piston 30. The needle holder 26 then abuts against the transverse wall 20 of the nipple member 19 and the ampule 15 is thus displaced alone so that the web 32 of the front end partition or piston 30 is pierced by the rear end 27B of the needle 27 (FIG. 3). The compartment C is then in communication with the hollow needle 27 and the medicated substance contained in this compartment is injected into the patient's body, under the pressure exerted by the drive member 70, via a recess 3 in the front end partition or piston 30.

When the first intermediate partition or piston 37 approaches the front end partition or piston 30 compartment C is practically empty. The valve operator 50 of the valve member 46 then abuts the actuator or abutment 34. The abutment 34 is fixed and therefore under the thrust of the drive member 70 the valve member 46 is dislodged from its axial recess 45 in the first intermediate partition or piston 37 so that compartment C1 is brought into communication with the hollow needle 27 via the first intermediate partition or piston 37 and the front end partition or piston 30.

When the compartment C1 is in turn practically empty the valve operator 50 of valve member 46 in the second intermediate partition or piston 37 comes into abutment against valve member 46 of the first intermediate partition or piston 37 so that, as shown in FIG. 3, the valve member 46 is dislodged from its axial recess 45 thereby bringing the third intermediate compartment C2 into communication with the hollow needle 27, via intermediate partitions or pistons 37 and 38 and the front end partition or piston.

It will be appreciated that the automatic syringe permits the injection of a plurality of different medicated substances in metered quantities and in succession.

Once the injection of the medicated substances is completed the ampule 15 may be discarded whereas the drive mechanism may be reused after being recocked.

Of course the present invention is not intended to be limited to the illustrated and described embodiment but on the contrary admits of various modifications and alternatives understood by those skilled in the art without departing from the spirit and scope of the present invention.

What I claim is:

1. An ampule for an automatic hypodermic syringe comprising at least two axially aligned and hermetically separated compartments adapted to contain respective medicated substances, a nipple member disposed at one end of the ampule, a needle holder mounted in said nipple member and supporting a hollow needle, said needle holder being displaceable between a standby position and an operative or injecting position, an intermediate partition normally hermetically separating said two compartments, said intermediate partition having a valve member, actuating means cooperable with said valve member after a first of said compartments is substantially emptied of its medicated substance to open a path of flow through said intermediate partition to bring the second of said compartments into communication with said hollow needle.

2. The ampule according to claim 1, wherein said needle holder also includes a support for a front end partition defining said actuating means for actuating said valve member when said first compartment is substantially emptied.

3. The ampule according to claim 2, wherein the front end partition which is adjacent said nipple member comprises a perforable central web adapted to be pierced by said hollow needle.

4. The ampule according to claim 3, wherein said actuating means and said valve member carried by said intermediate partition lie along the longitudinal axis of said ampule.

5. The ampule according to claim 1, wherein said intermediate piston comprises an axial recess with a pair of seats cooperable with complementary surfaces on the valve member to normally sealingly separate said compartments.

6. The ampule according to claim 5, wherein said valve seats are inclined in opposite directions so as to normally axially immobilize said valve member in said axial recess.

7. The ampule according to claim 5, wherein one of said seats is defined by a deformable annular lip.

8. The ampule according to claim 1, wherein there are two end partitions at the respective ends of said ampule and two said intermediate partitions disposed axially between said end partitions, to define three said compartments.

9. The ampule according to claim 8, wherein the valve member in the first mentioned intermediate partition is adapted to actuate the valve member in a second said intermediate partition after the second compartment between said intermediate partition is substantially emptied.

10. An automatic hypodermic syringe comprising a drive mechanism and an ampule, said ampule comprising a least two axially aligned and hermetically separated compartments adapted to contain respectively medicated substances, a nipple member disposed at one end of said ampule, a needle holder slidably mounted in said nipple member and supporting a hollow needle, said needle holder being slidable between a standby position and an operative injecting position, an intermediate partition normally sealingly separating said two compartments, said intermediate partition having a valve member, actuating means cooperable with said valve member after a first of said compartments is substantially emptied of its medicated substance to open a path of flow through said intermediate partition to bring the second of said compartments into communication with said hollow needle.

11. The ampule according to claim 1, wherein said needle holder is slidably mounted in said nipple member.

12. The ampule according to claim 11, wherein said nipple member is adapted to abut against an initially closed end of the ampule before the first compartment is empty.

* * * * *